(12) United States Patent
Kulesza

(10) Patent No.: US 10,314,777 B2
(45) Date of Patent: Jun. 11, 2019

(54) DELIVERY OF HYDROPHOBIC BIOACTIVE AGENTS

(71) Applicant: John E. Kulesza, Berlin, CT (US)

(72) Inventor: John E. Kulesza, Berlin, CT (US)

( * ) Notice: Subject to any disclaimer, the term of this patent is extended or adjusted under 35 U.S.C. 154(b) by 0 days.

(21) Appl. No.: 15/696,928

(22) Filed: Sep. 6, 2017

(65) Prior Publication Data

US 2017/0360689 A1    Dec. 21, 2017

Related U.S. Application Data

(63) Continuation of application No. 13/879,554, filed as application No. PCT/US2011/056558 on Oct. 17, 2011, now Pat. No. 9,782,341.

(60) Provisional application No. 61/393,615, filed on Oct. 15, 2010.

(51) Int. Cl.
| | | |
|---|---|---|
| *A61K 31/56* | (2006.01) | |
| *A61K 8/89* | (2006.01) | |
| *A61K 8/04* | (2006.01) | |
| *A61K 8/37* | (2006.01) | |
| *A61K 8/67* | (2006.01) | |
| *A61Q 19/08* | (2006.01) | |
| *A61K 47/34* | (2017.01) | |
| *A61K 9/00* | (2006.01) | |
| *A61K 31/07* | (2006.01) | |
| *A61K 31/573* | (2006.01) | |
| *A61K 9/06* | (2006.01) | |
| *A61K 9/10* | (2006.01) | |

(52) U.S. Cl.
CPC .............. *A61K 8/89* (2013.01); *A61K 8/042* (2013.01); *A61K 8/37* (2013.01); *A61K 8/671* (2013.01); *A61K 9/0014* (2013.01); *A61K 31/07* (2013.01); *A61K 31/573* (2013.01); *A61K 47/34* (2013.01); *A61Q 19/08* (2013.01); *A61K 9/06* (2013.01); *A61K 9/10* (2013.01)

(58) Field of Classification Search
None
See application file for complete search history.

(56) References Cited

U.S. PATENT DOCUMENTS

| | | |
|---|---|---|
| 5,891,470 A | 4/1999 | Rinaldi |
| 6,524,562 B2 | 2/2003 | Guskey |
| 7,807,625 B2 | 10/2010 | Majewski et al. |
| 2008/0070875 A1 | 3/2008 | Majewski et al. |
| 2008/0139518 A1 | 6/2008 | Purcell |

FOREIGN PATENT DOCUMENTS

| | | | |
|---|---|---|---|
| EP | 0910336 A1 | 4/1999 | |
| WO | 2009090495 A2 | 7/2009 | |
| WO | WO-2009090495 A2 * | 7/2009 | ........... A61K 9/0014 |

OTHER PUBLICATIONS

Silsoft ETS (Technical Data Sheet, http://www.momentive.com/products/showtechnicaldatasheet.aspx?id=14448, Sep. 17, 2009). (Year: 2009).*
Cellbone Technology (Dimethy Isosorbide, 2007, http://cellbone.com/DMI.htm).
Silsoft ETS (Technical Data Sheet, http://www.momentive.com/products/showtechniicaldatasheet.aspx?id=14448, Sep. 17, 2009).
Water Free Emulsions, Formulary, Creations Couleurs,Dreux, France (known to Applicant as of Jun. 10, 2015).

* cited by examiner

*Primary Examiner* — Dennis Heyer
*Assistant Examiner* — Daniel M Podgorski
(74) *Attorney, Agent, or Firm* — Dinsmore & Shohl LLP; Weston R. Gould

(57) ABSTRACT

A composition for delivery of a hydrophobic bioactive agent is provided that provides for a partially solubilized storage solution that upon exposure to the air results in a fully solubilized bioactive agent in a molecular form for optimal delivery to the skin of a subject. The composition is used for the therapeutic treatment or diagnosis of numerous skin conditions such as inflammation, and epidermal or musculoskeletal pain.

17 Claims, No Drawings

DELIVERY OF HYDROPHOBIC BIOACTIVE AGENTS

CROSS REFERENCE TO RELATED APPLICATIONS

This application is a continuation of U.S. application Ser. No. 13/879,554 filed Aug. 6, 2013, which is a 37 U.S.C. § 371 national phase of PCT/US2011/056558 filed Oct. 17, 2011 and claims priority to U.S. Provisional Application No. 61/393,615 filed Oct. 15, 2010.

FIELD OF THE INVENTION

This invention relates to compositions and methods for delivery of water insoluble or hydrophobic bioactive agents to the skin.

BACKGROUND OF THE INVENTION

Lipophilic skin care active agents such as retinoids are generally applied topically to reduce the appearance of aging, for other cosmetic purposes, or to treat a skin condition such as acne.

The comfort associated with application of topical agents is related in part to the rate of evaporation of the applied composition on the skin. A product with a slow evaporation rate could feel greasy on the skin whereas a product with an overly rapid evaporation rate feels either as if it has not been applied to the skin at all or leaves the user with the impression that not enough has been applied possibly leading to overuse. Combining topical agents with volatile silicones allows the proper evaporation rate to provide a pleasing application. Silicones, however, by themselves are poor solvents for hydrophobic organic active agents.

To address the poor solubility in silicones, delivery systems for these agents commonly require 35% or more organic solvent as a carrier to solubilize the active agent as well as provide suitability for combination with volatile compounds that provide pleasing application by the user. The prior art prefers alcohols such as ethyl alcohol as an organic solvent.

Many active agents contribute to thinning or drying of the skin. This problem is worsened by including significant levels of organic solvents that themselves can alter epidermal barrier lipids and contribute to skin irritation. Ethyl alcohol as used in the retinoid composition of U.S. Pat. No. 4,826,828 was believed to be the solution for topical delivery of hydrophobic agents. Ethyl alcohol, to the contrary, contributes to skin irritation and dryness. Thus, combining ethyl alcohol with potentially irritating active agents increases skin dryness leading to non-optimal use.

Thus, there exists a need for a hydrophobic active agent delivery system that provides pleasing application and does not contribute to toxicity.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

A composition suitable for delivery of a bioactive agent to the skin of a subject is provided. A composition includes a bioactive agent, a non-volatile solvent into which the bioactive agent is soluble, a carrier, and a thickener. A bioactive agent in some embodiments is a corticosteroid, hydroxy acid, antimicrobial, anti-inflammatory, or a combination thereof. A carrier is a compound that has sufficient volatility to vaporize upon application of the composition to the skin of a subject, and optionally at standard temperature and pressure.

A bioactive agent is appreciated to be present in the composition at a first concentration where the concentration of the bioactive agent increases upon volatilization of the carrier. The bioactive agent is optionally in molecular (solubilized) form, microcrystalline form, or partly in both forms. As such, a bioactive agent is optionally less than 100% in solution. In some embodiments, a bioactive agent is a corticosteroid such as halobetasol. Halobetasol is optionally present at 0.025 to 0.05 percent by weight.

A solvent is optionally dimethylisosorbide, ethoxydiglycol, or a combination thereof.

Some embodiments include an opacifier, illustratively titanium dioxide.

Processes for forming a composition are also provided that include dissolving a bioactive agent in a non-volatile solvent, and combining a carrier with the solvent such that the presence of said carrier places at least a portion of said bioactive agent in a crystalline state. A thickener optionally is added to the carrier prior to or following combining the carrier with the bioactive agent and non-volatile solvent.

Processes of treating one or more skin conditions are also provided. The processes include administering an inventive composition to a subject with a skin condition. The composition is optionally administered topically. Frequency of administration is optionally from one to three times daily. A skin condition is optionally musculoskeletal pain, inflammation, dryness, eczema, psoriasis, or rosaceous.

DETAILED DESCRIPTION

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes or compositions herein are described as an order of individual steps or using specific materials, it is appreciated that described steps or materials may be interchangeable such that the description of the invention includes multiple parts or steps arranged in many ways as is readily appreciated by one of skill in the art.

The invention has utility for efficient delivery of one or more hydrophobic bioactive agents to a subject. A composition is provided whereby a bioactive agent is not completely solubilized until application to the skin of a subject whereby upon evaporation of a volatile solvent the bioactive agent becomes fully solubilized to a molecular form. A composition includes:

A volatile carrier in which a bioactive agent is essentially insoluble;

A non-volatile solvent in which the bioactive agent is soluble; and

A thickener.

The bioactive agent is first dissolved in the non-volatile solvent, then that solution is added to the volatile carrier to create a system where the bioactive agent is partly in solution and partly in a microcrystalline state. The microcrystals are distributed uniformly within the gel created by the thickener. When this composition is applied to the skin surface, the volatile portion evaporates leaving essentially the bioactive agent, non-volatile solvent and thickener. The bioactive agent goes into solution and reaches optimal biological activity in molecular form. The non-volatile solvent can be used at a concentration such that the solution forming on the skin surface is optimally in a saturated or super-saturated state, enhancing percutaneous penetration in the skin.

One or more of several bioactive agents are used with the compositions. When the term bioactive agent is used herein, it is appreciated to be equally applicable to the singular one bioactive agent as well as to a plurality of bioactive agents. Some embodiments include a single bioactive agent only. Some embodiments include a plurality of bioactive agents.

As used herein the term "bioactive agent" refers to a molecule suitable for delivery to the skin or mucosal regions of a subject. Optionally, an active agent has pharmaceutical activity and is present for the treatment or prevention of a skin condition. Active agents are optionally low polarity molecules such as those having a hydrocarbon chain of three or more carbons, but may also comprise materials of higher polarity. Illustrative examples include retinol (vitamin A), retinal, retinyl ester, retinol, tretinoin (all-trans-retinoic acid), isotretinoin, adapalene, tazarotene, and 13-cis-retinoic acid, as well as a variety of esters and similar derivatives. A bioactive agent is optionally one or more esters and amides of 9-cis-retinoic acid such as those described in U.S. Pat. No. 5,837,728. A bioactive agent is optionally one or more of esters or amides of trans-retinoic acid such as those found in U.S. Pat. No. 4,055,659 (all-trans-retinoyloxyacetamide), U.S. Pat. No. 4,126,697 (4-(all-trans-retinoyloxyacetyl)-catechol), U.S. Pat. No. 4,126,698 (2-hydroxyethyl all-trans-retinoate), and U.S. Pat. No. 4,304,787 (benzyl all-trans-retinoate), as well as mixtures of these and other bioactive agents. A bioactive agent is optionally a retinoid such as those described in U.S. Patent Application Publication No: 2008/0139518.

A bioactive agent is not limited to vitamin A and its derivatives. One or more other bioactive agents are similarly suitable for inclusion in a composition as a bioactive agent. Illustrative examples include hydroxy acids; aromatic molecules such as benzoyl peroxide and resorcinol; antimicrobials such as azelaic acid, erythromycin, sodium sulfacetamide, tetracycline and derivatives, and clindamycin; antineoplastic agents and/or ophthalmic agents illustratively including 5-fluorouracil, doxorubicin, imiquimod, and sodium [o-(2,6-dichloranilino) phenyl] acetate; anti-viral agents illustratively ganciclovir, trifluorothymidine and related compounds; steroidal anti-inflammatory agents; non-steroidal anti-inflammatory agents illustratively flurbiprofen, ibuprofen, naproxen, indomethacin and related compounds; anti-mitotic drugs illustratively colchicine taxol and related compounds; drugs that act on actin polymerization illustratively phalloidin, cytochlasin B and related compounds; inhibitors of dihydropyrimidine dehydrogenase (DPD), thymidine phosphorylase (TP) and/or uridine phosphorylase (UP) enzyme inhibitors; ultraviolet light (UV) filters illustratively benzophenone derivatives such as oxybenzone, octocrylene, octyl methoxycinnamate, and avobenzone; radiation proactive agents illustratively methyluracils such as 6-methyluracil and 4-methyluracil; and immunomodulating molecules such as tacrolimus, and pimecrolimus; peptides (i.e. non-enzymatic protein); enzymes; amino acids, illustratively glutamate, glycine, alanine, valine, leucine, isoleucine, serine, threonine, arginine, lysine, aspartic acid, methionine, phenylalanine, tyrosine, proline, oxyproline, hidtidine, among other amino acids, both essential an non-essential known in the art, and derivatives thereof; growth factors, illustratively, epidermal growth factor, TGF-a, TGF-b, VEGF, among others known in the art; topical anesthetics, illustratively, benzocaine, butamben, dibucaine, lidocaine, oxybuprocaine, pramoxine, proparacaine, proxymetacaine, and tetracaine; and combinations thereof. A bioactive agent need not have pharmaceutical activity. Other bioactive agents are illustratively cosmetics such as pigments, dyes, and fillers.

A bioactive agent is optionally a hydroxy acid. Examples of hydroxy acids illustratively include beta hydroxyl acids such as salicylic acid, acetylsalicylic acid, and the like.

In some embodiments, a bioactive agent is a steroid or steroid derivative. Illustrative examples of steroids or steroid derivatives include the corticosteroids or corticosteroid derivatives. Examples of corticosteroids illustratively include hydrocortisone, hydrocortisone acetate, cortisone acetate, tixocortol pivalate, prednisolone, methylprednisolone, prednisone, betamethasone, betamethasone sodium phosphate, dexamethasone, dexamethasone sodium phosphate, fluocortolone, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, 17-aceponate, 17-buteprate, prednicarbate, flunisolide, fluticasone propionate, halobetasol, among others, and combinations thereof.

A bioactive agent is optionally a lipid such as those suitable for controlling perspiration. Lipids optionally have an HLB of less than 12, less than 8, or optionally less than 6. Illustrative examples of lipids include glyceryl monostearate, glyceryl monoisostearate, glyceryl monomyristate, glyceryl monoleate, diglyceryl monoisostearate, propylene of glycol monostearate, propylene glycol monoisostearate, propylene glycol monocaprylate, sorbitan monoisostearate, sorbitan monocaprylate, sorbitan monoisooleate, glyceryl monolaurate, glyceryl monocaprylate, glyceryl monocaprate, mixtures thereof or the like. Optionally, the lipid is glyceryl monolaurate, made available by suppliers like Fitz Chem Corporation under the name MONOMULS 90-L12.

A lipid optionally makes up from about 4 to about 35%, and optionally, from about 5 to about 20%, and optionally, from about 10 to about 15% by weight of the composition, based on total weight of the composition and including all values and ranges between 4% to 35%.

The compositions of the invention optionally include 0.005 to 1.0 weight percent retinol, in which case they are optionally applied directly to the skin, or supplied as more concentrated solution containing higher levels of active agent, in which case prior to application they are diluted optionally by means of a cosmetically acceptable carrier to a desired level such as 0.005 to 2.0 weight percent for retinol.

It is appreciated that an inventive composition optionally includes more than one bioactive agent. Optionally, 2, 3, 4, 5, 6, or more bioactive agents are present in an inventive composition. An active agent is optionally a prodrug that is converted to a desired active species optionally in the skin or layer thereof.

Optionally, a bioactive agent is present in less than 30 percent w/w amounts. Optionally, active agent is present at a weight percent of 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0.5, 0.1, 0.01, 0.001, 0.0001, any level in between or any range between 30% and 0.0001 percent by weight. Optionally, a bioactive agent is present at 20 percent w/w. Illustratively, when azelaic acid is an active agent it is present at 15 to 25 percent w/w. A vitamin A derivative is optionally present at 0.001 to 2 percent by weight. Imiquimod is optionally present at 3 to 8 percent by weight. Benzoyl peroxide is optionally present at 1 to 10 percent by weight. A steroid or steroid derivative is optionally included in a composition at 0.01 to 10% or more by weight. Optionally, a steroid is present at from 0.01 to 1% by weight, optionally 0.02 to 0.08% by weight, optionally 0.025 to 0.05% by weight. As examples of some embodiments, halobetasol is present at 0.025 to 0.05% by weight.

In some formulations of the invention, water is optionally minimized or eliminated to improve the stability of retinol and to minimize the potential for separation of the oil and water. Optionally, water is present at less than 2%. One of ordinary skill in the art will recognize that differing levels of active agent will be operable herein depending on the desired final amount of active agent at administration.

A bioactive agent delivery composition includes a carrier that is a volatile solvent. A volatile carrier that has a boiling point and heat of vaporization such that it will volatilize at one atmosphere at the temperature of the surface of the skin of a subject, illustratively, at or in excess of 32° C. A bioactive agent is optionally insoluble in a carrier. A bioactive agent is optionally soluble in a carrier at the level present in the composition such that when the bioactive agent and solvent are combined with the carrier, the entire portion of the bioactive agent remains in molecular form. A volatile carrier includes volatile compounds such as volatile silicones. Silicones are illustratively cyclic silicones or non-cyclic silicones. Examples of cyclic silicones illustratively include cyclic polydiorganosiloxanes, cyclotetradimethicones and cyclopentadimethicones. Linear organopolysiloxanes are illustratively alkyl-, alkoxy- or phenyldimethicones, and alkyl-, alkoxy- or phenyltrimethicones. Optionally, a carrier is an aliphatic volatile silicone. Aliphatic volatile silicones optionally have from two to six silicon atoms. Optionally, an aliphatic volatile silicone is a linear polyorganosiloxane such as a polyorganosiloxane with 2 to 6 silicon atoms, optionally, trisiloxane. Optionally, a carrier is ethyl trisiloxane. It is appreciated that an inventive composition optionally includes more than one carrier.

Volatile silicones optionally are lightweight carriers that evaporate on application and thus have an elegant, lightweight "feel" on the skin. Volatile silicones are typically limited in their ability to dissolve low polarity (i.e. usually greater than C7-C8)) organic compounds, illustratively, retinoids. For example, when relatively low therapeutic levels of retinol (0.1-0.2% w/v) are dissolved in cyclomethicone alone, hazy solutions result due to incomplete solubilization by the silicone fluid.

Some embodiments include a vehicle. A vehicle is optionally an organic polyhalogenic vehicle. Organic polyhalogenic vehicles are optionally those disclosed in U.S. Pat. No. 6,251,375. In particular instances, vehicles incorporate a halogen such as one or more fluorine atoms. In some specific instances, a vehicle is a perfluoro ether. In some particular instances, a vehicle is methoxynonafluorobutane, ethoxynonafluorobutane, or combinations thereof and available from 3M Specialty Materials, St. Paul, Minn. An organic polyhalogenic vehicle is optionally used as a substitute for a portion of a carrier in a composition. A vehicle optionally has a boiling point less than 78° C. Optionally, a vehicle has a boiling point below 65° C. A vehicle is optionally present at a final concentration of about 5 percent to 40 percent w/w. Optionally, a vehicle is present at from 15 percent to 25 percent w/w. Optionally, a vehicle is present at 20% w/w. It is appreciated that more than one vehicle is optionally present in an inventive composition. Optionally, 2, 3, 4, 5, 6, or more vehicles are present in an inventive composition.

Some embodiments of a composition are free of a vehicle. Optionally, a composition is free of an organic polyhalogenic vehicle.

A composition includes one or more non-volatile solvents that are suitable to solubilize a bioactive agent at a desired concentration. A non-volatile solvent is typically non-volatile at ambient temperatures and pressures on the surface of the skin. Illustrative examples of non-volatile solvents include but are not limited to dimethylisosorbide, ethoxydiglycol, glycerol, propylene glycol, isostearic acid, oleic acid, propylene glycol, trolamine, tromethamine, triacetin, sorbitan monolaurate, sorbitan monooleate, sorbitan monopalmitate, butanol, benzoic acid, butyl alcohol, dibutyl sebecate, diglycerides, dipropylene glycol, eugenol, fatty acids, isopropyl myristate, mineral oil, oleyl alcohol, vitamin E, triglycerides, sorbitan fatty acid surfactants, triethyl citrate, 1,2,6-hexanetriol, alkyltriols, alkyldiols, acetyl monoglycerides, tocopherol, alkyl dioxolanes, p-propenylanisole, anise oil, apricot oil, dimethyl isosorbide, alkyl glucoside, benzyl alcohol, bees wax, benzyl benzoate, butylene glycol, caprylic/capric triglyceride, caramel, cassia oil, castor oil, cinnamaldehyde, cinnamon oil, clove oil, coconut oil, cocoa butter, cocoglycerides, coriander oil, corn oil, coriander oil, corn syrup, cottonseed oil, cresol, cyclomethicone, diacetin, diacetylated monoglycerides, diethanolamine, diethylene glycol monoethyl ether, diglycerides, ethylene glycol, eucalyptus oil, fat, fatty alcohols, flavors, liquid sugarsm ginger extract, glycerin, high fructose corn syrup, hydrogenated castor oil, IP palmitate, lemon oil, lime oil, limonene, milk, monoacetin, monoglycerides, nutmeg oil, octyldodecanol, olive alcohol, orange oil, palm oil, peanut oil, PEG vegetable oil, peppermint oil, petrolatum, phenol, pine needle oil, polypropylene glycol, sesame oil, spearmint oil, soybean oil, vegetable oil, vegetable shortening, vinyl acetate, wax, 2-(2-(octadecyloxy)ethoxy)ethanol, benzyl benzoate, butylated hydroxyanisole, candelilla wax, carnauba wax, ceteareth-20, cetyl alcohol, polyglyceryl, dipolyhydroxy stearate, PEG-7 hydrogenated castor oil, diethyl phthalate, diethyl sebacate, dimethicone, dimethyl phthalate, PEG fatty acid esters, PEG-stearate, PEG-oleate, PEG laurate, PEG fatty acid diesters, PEG-dioleate, PEG-distearate, PEG-castor oil, glyceryl behenate, PEG glycerol fatty acid esters, PEG glyceryl laurate, PEG glyceryl stearate, PEG glyceryl oleate, hexylene glycerol, lanolin, lauric diethanolamide, lauryl lactate, lauryl sulfate, medronic acid, methacrylic acid, multisterol extract, myristyl alcohol, neutral oil, PEG-octyl phenyl ether, PEG-alkyl ethers, PEG-cetyl ether, PEG-stearyl ether, PEG-sorbitan fatty acid esters, PEG-sorbitan diisosterate, PEG-sorbitan monostearate, propylene glycol fatty acid esters, propylene glycol stearate, propylene glycol, caprylate/caprate, sodium pyrrolidone carboxylate, sorbitol, squalene, stear-o-wet, triglycerides, alkyl aryl polyether alcohols, polyoxyethylene derivatives of sorbitan-ethers, saturated polyglycolyzed C8-C10 glycerides, N-methyl pyrrolidone, honey, polyoxyethylated glycerides, dimethyl sulfoxide, azone and related compounds, dimethylformamide, N-methyl formamaide, fatty acid esters, fatty alcohol ethers, alkyl-amides (N,N-dimethylalkylamides), N-methyl pyrrolidone related compounds, ethyl oleate, polyglycerized fatty acids, glycerol monooleate, glyceryl monomyristate, glycerol esters of fatty acids, silk amino acids, PPG-3 benzyl ether myristate, Di-PPG2 myreth 10-adipate, honeyquat, sodium pyroglutamic acid, abyssinica oil, dimethicone, macadamia nut oil, limnanthes alba seed oil, cetearyl alcohol, PEG-50 shea butter, shea butter, aloe vera juice, phenyl trimethicone, hydrolyzed wheat protein, and combinations thereof.

The relative amounts of the non-volatile solvent and bioactive agent are dependent on the identity of the bioactive agent and the solvent. Optionally, the ratio of bioactive agent to non-volatile solvent is anywhere from 0.0001:1 to 1:1, or any value or range therebetween. Optionally, the ratio of bioactive agent to non-volatile solvent is from 0.01:1 to 0.1:1. Optionally, the ratio of bioactive agent to non-volatile solvent is from 0.02:1 to 0.2:1.

The relative amounts of non-volatile solvent and carrier varies depending on the exact amount of bioactive agent in the system. The ratios of the bioactive agent, non-volatile solvent(s), and carrier(s) is designed to provide a system such that the concentration of the bioactive agent is increased, optionally to a supersaturated level in the non-volatile solvent, upon vaporization of the carrier when the product is applied to the skin. In some embodiments, the composition includes a bioactive agent that is entirely in microcrystalline form, but is present at a level relative to the amount of non-volatile solvent that it will redissolve to the molecular form upon volatilization of the carrier. Thus, the relative ratios of the bioactive agent, the carrier and the non-volatile solvent create a system that promotes effective administration or exposure of the bioactive agent to the subject.

In some embodiments, the ratios of the bioactive agent, non-volatile solvent(s), and carrier(s) are designed to hold the bioactive agent just beyond or near the point of saturation prior to exposure to the air upon application to the skin or preparation for application to the skin or other use. The presence of the carrier in which the bioactive agent is not-soluble in the formulation of the composition prevents full solubilization of the bioactive agent. Upon exposure to the atmosphere or contact with the skin, the carrier evaporates promoting solubilization of the microcrystalline form of the bioactive agent in the non-volatile solvent that surprisingly drives effective administration of the bioactive agent to the subject. Thus, the relative ratios of the bioactive agent, the carrier and the non-volatile solvent create a system that promotes effective administration or exposure of the bioactive agent to the subject. It is appreciated that the relative amounts of bioactive agent, the carrier and the non-volatile solvent are readily appreciated by one of ordinary skill in the art. It is further appreciated that upon volatilization of the carrier the resulting formulation optionally does not form a solid, but remains in a lotion, cream, or other fluid form for ease of application to the skin as well as for optimal exposure of the bioactive agent to the skin.

In some embodiments, a bioactive agent is halobetasol in an amount from 0.001 to 1.0% by weight, or any value or range therebetween. Optionally, halobetasol is present in an amount ranging from 0.025 to 0.5% by weight. Optionally, halobetasol is present at 0.05% by weight.

In some embodiments, a bioactive agent is a vitamin A derivative such as a retinoid. As an example, some embodiments include hydroxyanasatil retinoate, a form of all-trans retinoate sold by Concert, LLC, Memphis, Tenn., optionally in an amount of 0.1 percent by weight. This material is insoluble at this concentration in the carrier sold under the tradename GRANSIL GTS, which is a mixture of ethyl trisiloxane and polysilicone-11. However, addition of the non-volatile solvent dimethyl isosorbide at 0.8% places the retinoate in a mixed state of solubilized material and crystalline material. Upon exposure to the environment for application to the skin, the carrier volatilizes allowing the crystalline retinoate to resolubilize in the solvent for increased penetration of the skin.

The inventive composition optionally includes other additives or pharmaceutical carriers illustratively including: stabilizers such as the anti-oxidant BHT; surfactants illustratively Laureth-4; anti-oxidants illustratively vitamins C and E, and Green tea extract (i.e. *Camellia sinensis*) or SILOX GT from Collaborative Labs, Stony Brook, N.Y.; and emollients illustratively the mixture or single components of the emollient sold under the brand name SYMREPAIR available from Symrise, Teterboro, N.J. One of ordinary skill in the art readily appreciates additives suitable for use with the present invention such as to provide desired flow characteristics, absorption, evaporation, delivery of active agent, conversion of a prodrug, or other desired characteristic.

The compositions of the invention are also optionally diluted to the appropriate bioactive agent level for application by using other topically acceptable compounds or vehicles which are optionally miscible with the bioactive agent(s) of the inventive compositions. Other cosmetic additives are optionally employed, either in the compositions of the invention or in those compositions when diluted with a suitable vehicle.

A composition optionally includes one or more thickeners. Illustrative examples of thickeners include dimethicone crosspolymers such as dimethicone/vinyl dimethicone crosspolymer and dimethicone/phenyl vinyl dimethicone crosspolymers, high molecular-weight silicone waxes, acrylic polymers that are soluble in silicones, and other thickeners known in the art that are soluble in a carrier. Illustrative examples of a thickener include polysilicone-11, and stearoxymethicone/dimethicone copolymer.

A composition optionally includes one or more opacifying agents. An opacifying agent is any agent known in the art compatible with the other components of a composition. Illustrative examples of opacifying agent include water-insoluble surface-active substances and polyoxyalkylene ethers, polymers and copolymers of styrene. Specific non-limiting examples of an opacifying agent include: titanium dioxide; aluminum caprylate; aluminum hydroxide hydrate; aluminum tristearate; attapulgite; calcium carbonate; calcium silicate; calcium sulfate; cellulose microcrystalline; cetyl alcohol; diatomaceous earth; dicalcium phosphate; glycol distearate; ethylene glycol distearate; iron powder; kaolin; magnesium carbonate; magnesium myristate; magnesium oxide; magnesium palmitate; magnesium silicate; (Z)-oleyl alcohol; petrolatum wax microcrystalline; polymethyl silsesquioxane; propylene glycol stearate; sasa senanensis leaf powder; silica; sodium polymethacrylate; solum fullonum; stearyl alcohol; talc powder; tricalcium phosphate; trimagnesium phosphate; zinc carbonate; zinc ricinoleate; opacifying agents listed in U.S. Pat. No. 4,009,139; and combinations thereof.

The compositions formulated as described herein are optionally topically applied to the skin at a concentration that results in application of a bioactive agent at a desired concentration following volatilization of the carrier. Illustratively, a composition optionally includes 0.005 to 1.0 weight percent retinol, optionally 0.01 to 0.50 weight percent. A bioactive agent is optionally supersaturated upon evaporation of the carrier. Thus, the maximum amount of active agent is limited only by the ability to provide a supersaturated solution created upon application.

An active agent is optionally applied in the areas where fine lines, wrinkles, dry or inelastic skin or large pores are observed as a condition. Optionally, a moisturizer is applied with or after application of the inventive compositions to enhance the tactile comfort associated with application of the compositions and to enhance the desired therapeutic outcome such as musculoskeletal pain reduction, wrinkle effacement, or other benefits achieved by the compositions. An improved characteristic of the inventive composition is that the use of additional moisturizers is not essential. As such, an inventive composition is optionally free of an additional moisturizer.

One or more moisturizers that are compatible with the carrier to a level of up to 35% by weight of the final formulation are optionally included. In some embodiments, a composition does not include a moisturizer. Moisturizers illustratively include petrolatum, ethylhexyl palmitate, cholesterol fatty acid ceramide, and squalene. The addition of one or more moisturizers is beneficial when the inventive composition is applied to previously dried skin or under conditions where dryness commonly occurs such as in cold climates, or winter months. Optionally, a moisturizing component is applied where the active agent itself has a drying effect such as when retinol or 5-fluorouracil is applied.

With daily application of a retinol containing composition, skin texture, color and tone will improve. Wrinkles and fine lines will be reduced with minimal irritant effects.

An inventive composition is optionally applied to the skin of a subject. A subject is optionally a patient. A subject is optionally a mammal such as humans, non-human primates, horses, goats, cows, sheep, pigs, dogs, cats, and rodents.

An inventive composition is optionally provided as a lotion, cream, gel, bar, ointment, or in pad form. Optionally, the composition is provided in a single use container the contents of which are applied directly to the stratum corneum of a subject or applied to an applicator pad for subsequent delivery to the subject.

A cooling effect is optionally observed upon topical application of the inventive composition. Cooling effect as used herein means reducing the temperature of skin, optionally, from about 1 to about 2° C. upon application. The cooling effect includes the effect that results from carrier or vehicle evaporation.

The inventive composition is optionally administered one to three times daily. Optionally, the inventive composition is administered once daily. Optionally, the inventive composition is administered weekly, biweekly, monthly, or any subdivision thereof. It is appreciated that the inventive composition is optionally administered for an amount of time suitable for efficacy of the active agent. Optionally, the inventive composition is administered for one to six weeks. Optionally, the inventive composition is administered indefinitely.

Numerous skin or systemic conditions are treatable, diagnosable, or preventable with the inventive compositions illustratively including acne, wrinkles, musculoskeletal pain, inflammation, dryness, eczema, psoriasis, actinic and nonactinic keratoses, rosaceous, among others, or combinations thereof. U.S. Pat. No. 3,932,665 describes retinal as a therapeutic agent in a method for treating acne by topical application. The topical administration of 5-fluorouracil for treatment of keratoses is described in U.S. Pat. No. 4,034,114. The inventive composition reduces the associated side effects that typically accompany topical or ophthalmologic administration of bioactive agents.

The inventive compositions are suitable for topical delivery of a bioactive agent to a subject optionally for the treatment of a skin condition. A skin condition is optionally treated by topically administering a composition to a subject with a condition or at risk for a condition such that the administering ameliorates or prevents the skin condition. With continued and regular use, a skin condition may be eliminated or prevented. Optionally, a composition is administered once to ameliorate, eliminate, or prevent a skin condition of a subject.

The inventive compositions optionally include a bioactive agent formulated in a carrier containing volatile silicone. With such a carrier, bioactive agent levels needed to achieve beneficial effects are minimized and the potential for irritant effects to the skin by a bioactive agent are greatly diminished.

Also provided are processes of storing one or more bioactive agents for subsequent topical administration to a subject or portion thereof. A process includes dissolving a bioactive agent in a non-volatile solvent and combining a carrier with the bioactive agent containing solvent. The presence of the carrier forces at least a portion, but less than 100% of the bioactive agent in a crystalline state.

The step of dissolving is by any method known in the art such as by stirring, vortexing, use of a physical mixing apparatus, or other known method. A solvent is optionally heated above room temperature for effective and complete solubilization of the bioactive agent. The amount of heat added is limited only by the stability of the components of the composition.

A process for storing one or more bioactive agents optionally includes the step of adding a thickener to the composition. A thickener is optionally added prior to dissolving a bioactive agent or subsequent thereto. Optionally, a thickener is added following combining a carrier with the solvent. The addition of a thickener creates a smooth, cream appearance and consistency to the composition.

One or more bioactive agents are optionally stored in the compositions in a state that is less than 100% in solution with the proviso that at least a portion of the bioactive agent is in a molecular state (i.e. solubilized). In a composition for storage of a bioactive agent or otherwise, a bioactive agent is optionally greater than 50, 55, 60, 65, 70, 75, 80, 85, 90, 95, 96, 97, 98, or 99 percent in molecular form.

A composition for storing one or more bioactive agents is optionally placed in an inert atmosphere. The term "inert" is appreciated to mean that the atmosphere or component thereof will not react with a bioactive agent. Illustrative examples of an inert atmosphere include nitrogen, argon, neon, or other inert gas known in the art.

A composition is optionally placed in a container that is opaque such that the composition is kept in minimal light conditions.

Various aspects of the present invention are illustrated by the following non-limiting examples. The examples are for illustrative purposes and are not a limitation on any practice of the present invention. It will be understood that variations and modifications can be made without departing from the spirit and scope of the invention.

Example 1

A retinoid delivery composition is formulated to include the following ingredients as listed in Table 1 as Formula A.

TABLE 1

Formula A

| Ingredient (INCI name/Brand name) | % w/w (final) | Supplier |
|---|---|---|
| Phase A | | |
| Diethyl sebacate | 2.4 | Ivanhoe Industries |
| Dimethyl isosorbide/Arlasolve DMI | 0.8 | Croda |
| Hydroxyanasatil retinoate/MDI 403 | 0.1 | Concert LLC |
| Phase B | | |
| Diethyl sebacate | 2 | Ivanhoe Industries |
| Tetrahexyldecyl ascorbate/BV-OSC | 1 | Barnet |
| Tocopherol USP | 0.5 | DSM |
| Laureth-4/Brij 30 | 0.5 | Croda |
| Phase C | | |
| Ethyl Trisiloxane (and) Polysilicone-11/Gransil GTS | 92.7 | Grant Industries |

To form the retinoid delivery composition of Table 1, the following process is preformed at standard temperature (approx. 25° C.) and pressure (1 atm) in the absence of any heating or cooling. A suitably sized kettle is loaded with Phase A ingredients in the order shown in Table 1. These are propeller mixed (non-vortex) to dissolve all ingredients and create a clear solution. Each Phase B ingredient is added to Phase A and mixed until completely dissolved. Separately, the Phase C ingredient is loaded into a suitably sized Kettle (Main Batch). The Phase A+B is slowly added to Phase C at a rate no faster than 5% of the weight of A+B per minute. The composition is mixed until uniform with slow side-sweep agitation. Mixing is stopped when a homogeneous gel is obtained. The composition is protected from light by transfer to a suitably sized container with a polyethylene liner.

Retinoid is present in the final formula partly in solution and partly in the form of microcrystals suspended in the silicone elastomer gel. Microcrystals form immediately after compounding because retinoid solubility in Phase A+B+C is less than in Phase A+B. This creates a haze. After product application to the skin surface, evaporation of the volatile silicone portion of the vehicle causes the microcrystalline retinoid to redissolve in the non-volatile portion of the vehicle remaining on the skin surface.

The composition is tested for contamination and physical properties as shown in Table 2.

TABLE 2

| Property | Result |
|---|---|
| Appearance: | Translucent pale Yellow Gel |
| Odor: | Mild characteristic |
| Non-Volatile matter wt. % (105° C., 3 hrs, 1.5 g, gravity oven) | 14.7-16.1 |
| pH: | n/a (anhydrous) |
| Viscosity: (200,000-250,000 cPs Apparatus: Brookfield DV-I+, Spindle T-E, 0.3 rpm, 1.0 min) | To match sample |
| Microbial Testing: | |
| Total Plate Count | NMT 100/gram |
| Salmonella spp. | Negative |
| E. coli | Negative |
| S. aureus | Negative |
| A. niger | Negative |
| Total yeast & molds | NMT 100/gram |

Example 2

The composition of Example 1 is reformed with varying concentrations of retinoid by also adjusting the relative concentration of Ethyl Trisiloxane and Polysilicone-11. The resulting compositions are listed in Table 3:

TABLE 3

| Formula | Retinoid (% w/w) |
|---|---|
| B | 0.005 |
| C | 0.01 |
| D | 1.0 |

Example 3

A corticosteroid containing composition is formed as in Table 4 as per Formula E.

TABLE 4

Formula E

| Ingredient (INCI name/Brand name) | % w/w (final) | Supplier |
|---|---|---|
| Phase A | | |
| Exoxydiglycol/Transcutol | 2.0 | Gattefosse |
| Halobetasol propionate | 0.05 | — |
| Phase B | | |
| PPG-3 Benzyl ether myristate/Crodamol STS | 2.5 | Croda |
| Titanium dioxide (and) Triethoxy caprylylsilane/BDT-11S2 | 0.3 | Kobo Products |
| Phase C | | |
| Cyclopentasiloxane (and) Petrolatum (and) Stearoxymethicone/Dimethicone Copolymer (and) Dimethicone/Gransil GI CD-10P | 85.15 | Grant Industries |
| Dimethicone (and) Polysilicone-11 (and) Petrolatum/Gransil DMG-20P | 10.0 | Grant Industries |

To form the halobetasol composition of Formula E, the following process is preformed at standard temperature (approx. 25° C.) and pressure (1 atm) in the absence of any heating or cooling. A suitably sized kettle is loaded with Phase A ingredients in the order shown in Table 4. These are propeller mixed (non-vortex) to dissolve all ingredients and create a clear solution. In a separate kettle, the Phase B ingredients are combined and propeller mixed (non-vortex) to create a uniform dispersion. The Phase A and Phase B are then combined with continuous non-vortex mixing. Separately, the Phase C ingredients are loaded into a suitably sized kettle and blended with a slow, side-sweep mixing until uniform. The Phase A+B is slowly added to Phase C at a rate no faster than 5% of the weight of A+B per minute. The composition is mixed until uniform with slow side-sweep agitation. Mixing is stopped when a homogeneous cream is obtained. The composition is transferred to a suitably sized container for storage.

The composition is tested for contamination and physical properties as shown in Table 5.

TABLE 5

| {{Property}} | {{Result}} |
| --- | --- |
| Appearance: | Glossy, white soft cream |
| Odor: | Mild characteristic |
| Non-Volatile matter wt. % (105° C., 3 hrs, 1.5 g, gravity oven) | 34.0-38.0 |
| pH: | n/a (anhydrous) |
| Viscosity: (200,000-250,000 cPs Apparatus: Brookfield DV-I+, Spindle T-E, 0.3 rpm, 1.0 min) | To match sample |
| Microbial Testing: | |
| Total Plate Count | NMT 100/gram |
| *Salmonella* spp. | Negative |
| *E. Coli* | Negative |
| *S. Aureus* | Negative |
| *A. Niger* | Negative |
| Total yeast & molds | NMT 100/gram |

Example 4

The formula of Example 3 is adjusted with varying concentrations of halobetasol. The relative amounts of Phase C ingredients are adjusted to form 100% w/w depending on the desired amount of halobetasol. The following formulas are created.

TABLE 6

| Formula | Halobetasol (% w/w) |
| --- | --- |
| F | 0.025 |
| G | 0.01 |
| H | 0.03 |

Example 5

A topical anesthetic containing composition is formed as in Table 7 as per Formula I.

TABLE 7

Formula I

| {{Ingredient (INCI name/Brand name)}} | {{% w/w (final)}} | {{Supplier}} |
| --- | --- | --- |
| Phase A | | |
| Exoxydiglycol/Transcutol | 2.0 | Gattefosse |
| lidocane | 4.0 | — |
| Phase B | | |
| PPG-3 Benzyl ether myristate/Crodamol STS | 2.5 | Croda |
| Titanium dioxide (and) Triethoxy caprylylsilane/BDT-11S2 | 0.3 | Kobo Products |
| Phase C | | |
| Cyclopentasiloxane (and) Petrolatum (and) Stearoxymethicone/Dimethicone Copolymer (and) Dimethicone/Gransil GI CD-10P | 81.2 | Grant Industries |
| Dimethicone (and) Polysilicone-11 (and) Petrolatum/Gransil DMG-20P | 10.0 | Grant Industries |

Example 6

A corticosteroid containing composition is formed as in Table 8 as per Formula J.

TABLE 8

Formula J

| {{Ingredient (INCI name/Brand name)}} | {{% w/w (final)}} | {{Supplier}} |
| --- | --- | --- |
| Phase A | | |
| Exoxydiglycol/Transcutol | 2.0 | Gattefosse |
| Promoxine HCL (and) hydrocortisone (1% each) | 2.0 | — |
| Phase B | | |
| PPG-3 Benzyl ether myristate/Crodamol STS | 2.5 | Croda |
| Titanium dioxide (and) Triethoxy caprylylsilane/BDT-11S2 | 0.3 | Kobo Products |
| Phase C | | |
| Cyclopentasiloxane (and) Petrolatum (and) Stearoxymethicone/Dimethicone Copolymer (and) Dimethicone/Gransil GI CD-10P | 83.2 | Grant Industries |
| Dimethicone (and) Polysilicone-11 (and) Petrolatum/Gransil DMG-20P | 10.0 | Grant Industries |

Example 7

Patients presenting with acne to a dermatologist provide informed consent to a split face test comparing Formula A of Example 1 with a commercially available benzoyl peroxide topical acne treatment of equal active ingredient concentration (STRIDEX POWER PADS, Blistex, Inc. Oak Brook, Ill.).

Fifteen females aged 20 to 39 apply Formula A to one side of their faces and the benzolyl peroxide comparator to the other side once daily for two weeks. Each subject is asked to record any side effects such as dryness, irritation, and perceived skin clarification. Both the Formula A and the comparator demonstrate similar skin clarification. Subjects report less irritation and improved skin condition on the Formula A treated side relative to comparator.

Example 8

A split face test is performed by using Formula A or a comparator as follows. Twelve females aged 20 to 59 apply Formula A to one side of their faces and comparator to the other side once daily for eight weeks. The comparator is made containing 46.3% Cyclomethicone-Tetramer; 35% Alcohol SD 40B Anhydrous; 5% Ethylhexyl Palmitate; 5% Octyl Dimethyl PABA; 2% Benzophenone-3; 2% Demineralized Water; 2% Neopentyl Glycol Dicaprate; 1.5% Ethyl Cellulose K5000; 0.22% Butylated Hydroxytoluene; and 1% Retinoid Blend. The comparator is prepared essentially as described in U.S. Pat. No. 4,826,828.

Thin shavings of the skin on each side of the face are taken before the test begins and after the eight week test period. The skin shavings after the test are in better condition than those before the test in all twelve women in the Formula A group and in nine of the twelve women in the comparator group. The skin of all women is both thicker and more organized after the test than before. All women in the Formula A group report improved moisture in the tested skin whereas the comparator group issues complaints of drying and cracking of the tested skin areas.

Example 9

A split face test is performed by using Formula A or the comparator of Example 5 as follows. Twelve females aged 20 to 59 apply Formula A to one side of their faces and comparator to the other side once daily for eight weeks. Thin shavings of the skin on each side of the face are taken before the test begins and after the eight week test period. The skin shavings after the test are in better condition than those before the test in all twelve women in the Formula A group and in nine of the twelve women in the comparator group. The skin of all women is both thicker and more organized after the test than before. All women in the Formula A group report improved moisture in the tested skin whereas the comparator group issues complaints of drying and cracking of the tested skin areas.

Example 10

Ten patients of varying ages ranging from 10 to 17 years, each diagnosed with atopic dermatitis have informed parental consent to have the composition of Formula E applied topically. Subjects present with moderate pruritus daily, extensive erythema, excoriation and induration/papulation on extremities. The composition of Formula E is topically applied once daily for two weeks. Subjects report reduction in itching and reduction in erythema within two days.

Example 11

Twelve subjects each presenting with 3-5 acute acne lesions on the face are used to determine the effectiveness of Formulas E-H (three subjects per formula). A selected patch of effected skin is used for the placement of a circular patch of sufficient dimension to cover the lesion of one of Formulas A-H. The selected formulation is applied one to two times per day on the selected lesions. Each treatment site is evaluated after 4, 8 and 24 hours by a clinician to evaluate the lesion/pimple redness (erythema). The conditions of each of the affected areas with applied halobetasol containing formula are alleviated.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A composition for topical delivery of a bioactive agent to a subject comprising:
    a bioactive agent selected from the group consisting of a corticosteroid and a hydroxy acid;
    a non-volatile solvent into which said bioactive agent is soluble, said solvent selected from the group consisting of dimethylisosorbide, ethoxydiglycol, and a combination thereof;
    a silicone in which said bioactive agent is insoluble, said silicone volatile at standard temperature and pressure; and
    a dimethicone crosspolymer thickener;
    said bioactive agent, said solvent, and said silicone present at concentrations to place said bioactive agent in a saturated or super-saturated state in said composition such that a portion of said bioactive agent is in a crystalline state.

2. The composition of claim 1 wherein said silicone is ethyltrisiloxane.

3. The composition of claim 1 wherein said bioactive agent is a corticosteroid.

4. The composition of claim 1 wherein said bioactive agent is halobetasol.

5. The composition of claim 4 wherein said halobetasol is present at 0.025 to 0.05 percent by weight.

6. The composition of claim 1 wherein said bioactive agent is a hydroxy acid.

7. The composition of claim 6 wherein said hydroxy acid is salicylic acid or acetylsalicylic acid.

8. The composition of claim 1 further comprising an opacifier.

9. The composition of claim 8 wherein said opacifier is titanium dioxide.

10. A process of forming the composition of claim 1 comprising:
    dissolving a bioactive agent in a non-volatile solvent into which said bioactive agent is soluble;
    combining said silicone with said solvent following said step of dissolving, the presence of said silicone placing at least a portion of said bioactive agent in a crystalline state.

11. The process of claim 10 further comprising adding a thickener.

12. The process of claim 11 wherein said step of adding creates a white cream.

13. A process of treating a skin condition comprising: administering the composition of claim 1 to a subject, wherein said skin condition is musculoskeletal pain, inflammation, dryness, eczema, psoriasis, or rosaceous.

14. The process of claim 13 wherein said administering is topically.

15. The process of claim 13 wherein said administering is from one to three times daily.

16. The process of claim 13 wherein said skin condition is inflammation and said bioactive is halobetasol.

17. A composition for topical delivery of a bioactive agent to a subject consisting essentially of:
    a bioactive agent selected from the group consisting of a corticosteroid and a hydroxy acid;
    a non-volatile solvent into which said bioactive agent is soluble, said solvent selected from the group consisting of dimethylisosorbide, ethoxydiglycol, and a combination thereof;
    a silicone in which said bioactive agent is insoluble, said silicone volatile at standard temperature and pressure; and
    a dimethicone crosspolymer thickener;
    said bioactive agent, said solvent, and said silicone present at concentrations to place said bioactive agent in a saturated or super-saturated state in said composition such that a portion of said bioactive agent is in a crystalline state.

* * * * *